(12) United States Patent
Boumsellek

(10) Patent No.: US 9,863,914 B2
(45) Date of Patent: Jan. 9, 2018

(54) MINIATURE QUADRUPOLE ARRAYS USING ELECTRON MULTIPLICATION DETECTORS

(71) Applicant: Implant Sciences Corporation, Wilmington, MA (US)

(72) Inventor: Said Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 0 days.

(21) Appl. No.: 14/808,291

(22) Filed: Jul. 24, 2015

(65) Prior Publication Data

US 2017/0023524 A1    Jan. 26, 2017

(51) Int. Cl.
  *G01N 27/62* (2006.01)
  *H01J 49/00* (2006.01)
  *H01J 49/42* (2006.01)

(52) U.S. Cl.
  CPC .......... *G01N 27/62* (2013.01); *H01J 49/0009* (2013.01); *H01J 49/0013* (2013.01); *H01J 49/42* (2013.01); *H01J 49/4215* (2013.01)

(58) Field of Classification Search
  CPC .... G01N 30/64; G01N 27/624; G01N 33/483; G01N 27/62; H01L 21/31116; G01R 19/0061; G01R 27/2641; H01J 49/0009; H01J 49/0013; A61N 1/0484; A61N 1/0408; A61N 1/0452; A61N 1/0472

USPC ....... 324/464, 600, 643–654, 717, 122, 705, 324/671, 693, 525; 607/2–3
  See application file for complete search history.

(56) References Cited

U.S. PATENT DOCUMENTS

| | | | |
|---|---|---|---|
| 5,719,393 A | 2/1998 | Chutjian et al. | |
| 6,239,429 B1 | 5/2001 | Blessing et al. | |
| 6,923,902 B2 * | 8/2005 | Ando | F01N 3/0842 204/424 |
| 2013/0009051 A1 * | 1/2013 | Park | H01J 49/063 250/282 |
| 2013/0240726 A1 * | 9/2013 | Hasegawa | H01J 49/4255 250/288 |

* cited by examiner

*Primary Examiner* — Melissa Koval
*Assistant Examiner* — Trung Nguyen
(74) *Attorney, Agent, or Firm* — Muirhead and Saturnelli, LLC

(57) ABSTRACT

A gas sensor includes a first chamber containing a plurality of evenly spaced rods having voltages applied thereto to cause gas ions in the first chamber to move in a direction from a first end of the first chamber to a second end of the first chamber and a second chamber coupled to the second end of the first chamber and having at least one ion detector, where ions pass from the first chamber to the second chamber through a plurality of channels between the first chamber and the second chamber and are detected by the at least one ion detector. The voltages applied to the rods may include a first voltage applied to a first subset of the rods and a second voltage applied to a second subset of the rods, each of first and second voltages containing a DC component and an AC component.

19 Claims, 5 Drawing Sheets

MINIATURE QUADRUPOLE ARRAYS USING ELECTRON MULTIPLICATION DETECTORS

TECHNICAL FIELD

This application relates to the field of quadrupole mass filters and more particularly to the field of miniature quadrupole mass filter arrays.

BACKGROUND OF THE INVENTION

Quadrupole residual gas sensors are known and are used for detecting the presence and measuring the quantity of specific gases within a chamber in vacuum conditions, e.g., at pressures of $1 \times 10^{-5}$ Torr or below. A conventional quadrupole residual gas sensor includes four parallel rods, with equal lengths, precisely arranged and mounted on a ceramic base in a square configuration, thus forming a quadrupole, with an open area, or channel, at the center and extending the full length, of the rods. An electron source generates electrons at one end of the quadrupole which collide with, and ionize, some of the ambient gas molecules in the chamber. Some of these ions are then injected into the channel for mass analysis prior to reaching a collector positioned at the other end of the quadrupole. The ions that impact upon the collector generate a voltage potential upon the collector proportional to the number of ions and thus proportional to the population of gas molecules within the chamber. When the collector is connected to external circuitry, a current, proportional to the amount of ions impacting upon the collector is thereby generated.

Within the channel, ions are filtered according to their mass-to-charge ratio by applying a combination of AC and DC voltages of the same polarity to diagonally opposed rods. AC and DC voltages of the same amplitude but of the opposite polarity are applied to the other diagonally opposed rods. Voltages, applied on the four parallel rods of the quadrupole, are tuned to generate an electric field in the channel between the four rods which permits only ions with a specific mass-to-charge ratio to trail the full length of the channel down to the collector. Ions with other mass-to-charge ratios are pulled by the electric field from the channel to one of the four parallel rods and neutralized. Hence, by tuning the voltages on the rods for different mass-to-charge ratios, and by analyzing the current generated by ions impacting on the collector at these voltages, the quadrupole can be used to detect the presence of different gases within a chamber under low pressure or vacuum conditions. The ability to sense these gases is useful for a wide range of applications including planetary exploration, semiconductor chip manufacturing, industrial processing, environmental monitoring, petrochemical and shale gas applications.

In many applications where there is a need to determine what gases exist in a chamber, the pressure in the chamber is substantially higher than the pressures necessary to operate the prior art sensor. For example, in the thin film deposition techniques used in the manufacture of semiconductor devices, the films are often deposited in chambers where the pressure may even be two orders of magnitude greater than the pressure needed to operate the above-described prior art sensors. However, to maximize the sensitivity of the sensor, length the ions must travel in the channel to the collector must be less than the mean free path of the ions. The mean free path of an ion is the mean distance the ion will travel in a straight line through its environment prior to colliding with another molecular particle. The channel length must, preferably, be less than the mean free path of the particle to thereby minimize the likelihood of an ion, with the tuned mass-to-charge ratio, colliding with another particle and being deflected out of the channel or neutralized. Tuned ions which are deflected in this manner will not impact upon the collector, resulting in a lower current being detected at the collector. The mean free path of a particle, such as an ion, can be calculated by a well known formula in which the mean free path is inversely proportional to the ambient pressure of the environment that the particle is in. Hence, conventional four rod (each rod is approximately 15 cm long and 1 cm in diameter) quadrupole residual gas sensors operate at relatively low pressures, e.g., $5 \times 10^{-5}$ Torr, to be able to obtain a mean free path greater than the length of the channel between the ion source and the collector.

One way to provide a quadrupole filter that allows operation at higher pressure is to miniaturize components of the filter to shorten the distance the ions travel. Any miniaturization effort results in an unavoidable reduction of instrument sensitivity due to the smaller acceptance area for the ions to be mass analyzed. Assembling arrays of quadrupoles to operate in parallel is one way to recovered some of the lost sensitivity due to miniaturization. Although this was suggested several decades ago, arrays of quadrupoles were difficult to assemble using conventional fabrication techniques. This has been addressed using a low cost glass-to-metal seal technology whereby the rods are held a glass chassis and voltages of opposite polarity are connected to alternating rods using thin photo-etched plates, as described in U.S. Pat. No. 5,613,294 to Ferran. The patent discloses a gas sensor having an array of quadrupoles (nine of them) formed by positioning a 4×4 array of rods (averaging 15 mm in length and 1 mm in diameter); a total of 16 in a matrix-like pattern.

The quadrupole array disclosed by Ferran uses a Faraday cup to detect ions of interest that reach the end of the chamber containing the rods. While detection with a Faraday cup is useful in many situations, in some cases it may be more desirable to use a different, more sensitive, detector, such as an electron multiplier. Electron multiplication based detectors such an electron multiplier and micro-channel plates contain a highly resistive coating on their internal surface. Incoming charged particles (e.g. ions and electrons) photons (e.g. UV and x-rays) release electrons upon colliding with the surface, via a secondary emission process, which triggers an avalanche process releasing more and more electrons. These electrons are channeled toward the exit via a high voltage bias between the entrance and the exit of the detector. The electron-to-ion conversion also called gain can achieve several orders of magnitude depending on the applied voltage.

However, because of miniaturization and the plurality of rods attached to the end of the sensor chassis, the quadrupole array disclosed by Ferran does not accommodate an electron multiplier.

Accordingly, it is desirable to provide a miniature quadrupole array like that taught by Ferran that can use an electron multiplier to detect gas ions of interest, possibly at much lower concentrations.

SUMMARY OF THE INVENTION

According to the system described herein, a gas sensor includes a first chamber containing a plurality of evenly spaced rods having voltages applied thereto to cause gas ions in the first chamber to move in a direction from a first end of the first chamber to a second end of the first chamber and a second chamber coupled to the second end of the first chamber and having at least one ion detector, where ions pass from the first chamber to the second chamber through a plurality of channels between the first chamber and the second chamber and are detected by the at least one ion detector. The voltages applied to the rods may include a first voltage applied to a first subset of the rods and a second voltage applied to a second subset of the rods, each of first and second voltages containing a DC component and an AC component. The DC components of the first and second voltages may be the same and the AC components of the first and second voltages have a same frequency and magnitude and a relative phase of 180 degrees and the magnitude of the AC components may be approximately six times a magnitude of the DC components. The at least one ion detector may include an electron multiplier or a micro-channel plate. The at least one ion detector may be on-axis or off-axis. The gas sensor may also include a Faraday cup provided in the second chamber. The at least one ion detector may be off-axis.

BRIEF DESCRIPTION OF THE DRAWINGS

Embodiments of the system are described with reference to the several figures of the drawings, noted as follows.

DETAILED DESCRIPTION OF VARIOUS EMBODIMENTS

Figure 1:
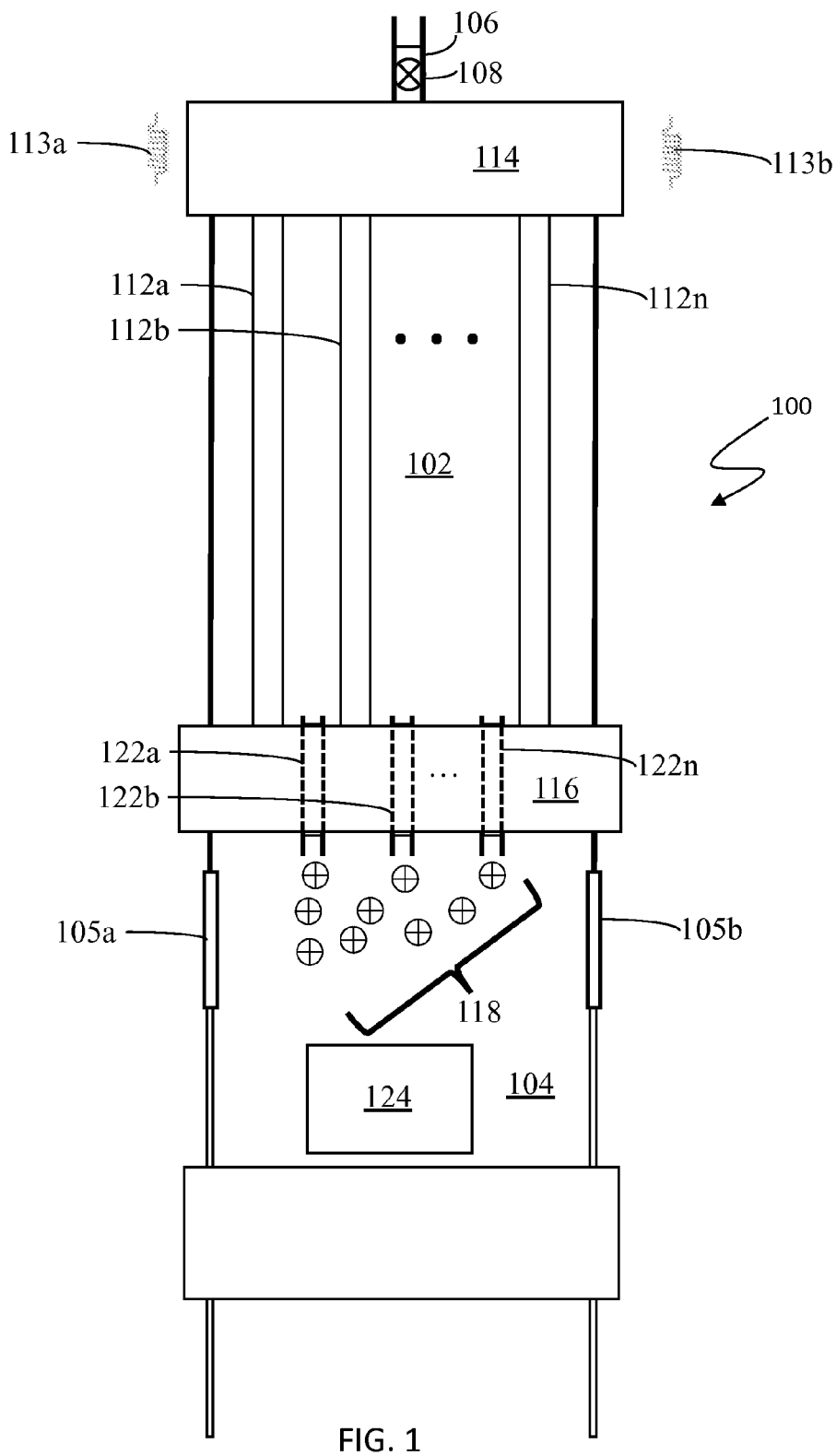
FIG. 1 is schematic diagram showing a miniature quadrupole mass filter arrays using with two chambers according to an embodiment of the system described herein.

Referring to FIG. 1, a quadrupole array gas sensor 100 has a first chamber 102 and a second chamber 104. The chambers 102, 104 are maintained at a vacuum (e.g., $1.5 \times 10^{-2}$ Torr or less) to facilitate detection of ions, as described herein. The chambers 102, 104 may be connected by airtight sleeves 105a, 105b. The chamber 102 is similar to the chamber used with the quadrupole array gas sensor of U.S. Pat. No. 5,613,294 to Ferran, which is incorporated by reference herein but features new ion transport channels embedded in the same glass chassis used to support rods and other components including metal pins intended to provide mechanical support of certain electrodes and apply appropriate voltages to them. An inlet 106 may be used to control the entry of gas to be analyzed by the sensor 100. A valve 108 at the inlet 106 opens to allow gas to enter the chamber 102 and closes to seal the chamber 102.

The chamber 102 includes a plurality of embedded rods 112a-112n that form a quadrupole array. In an embodiment herein, there are sixteen of the rods 112a-112n evenly spaced in a 4×4 array, but of course the system described herein may be implemented with any number of rods. In an embodiment herein, a first bus (not shown) receiving a first voltage and a second bus (not shown) receiving a second voltage are each respectively connected to eight of the sixteen rods 112a-112n so that, in any single quadrupole array element (group of four adjacent ones of the rods 112a-112n that form a square) the same voltage is applied to ones of the rods 112a-112n mounted diagonally from one another.

In an embodiment herein, each of the chambers 102, 104 may be configured from a hollow cylindrical metal body or casing having a solid glass seal formed therein to provide a gas-tight seal. Each of the chambers 102, 104 may have a diameter on the order of ⅝ inch and may be approximately ½ inch to ⅝ inches long. The material selected for the glass seal may be selected so that after assembly of the sensor 100, the glass seal securely retains the rods 112a-112n and other components in structurally stable positions and orientations. Furthermore, the material used for the glass seal may be selected to provide a vacuum tight seal with the rods 112a-112n and other components as well as with interior walls of the casing. The material used to form the glass seal may be a pre-formed glass blank or glass bead having a circular disk shape and having holes for each of the rods 112a-112n and other components. The pre-formed glass bead may be heated causing the glass to melt into the hardened glass seal which securely bonds to each of the rods 112a-112n and other components as well as to interior walls of the casing. The glass bead used to form the hardened glass seal may be selected to have thermal coefficients similar to the thermal coefficients of the base casing and having a suitable behavior when heated in an oven. Various types of glass may be used for the glass bead depending upon the other materials in the sensor 100 and depending upon the temperature range of the expected use of the sensor 100. For example, in an embodiment, the casing may be stainless steel and the glass bead may be a barium alkali glass having a relatively high temperature coefficient close to the temperature coefficient of stainless steel.

The voltages applied to the rods 112a-112n may have both an AC component and a DC component. The DC component of the first and second voltages may provide a constant DC voltage potential of, for example, fifty five volts DC at a center of a channel formed by a quadrupole array element (group of four of the rods 112a-112n, described above). An AC component of the first and second voltages may have a same amplitude and frequency, however, the first and second voltages may have a 180 degree phase difference from each other. Thus, at any one time, the sum of the AC components of the first voltage and the second voltage may equal zero. Furthermore, the AC and DC voltages may be selected so that the peak-to-peak value of the AC component is approximately six times the value of the DC component. In an embodiment herein, the AC and DC components may be respectively varied so long as 55 volts DC is still maintained in the center of the channel formed by each quadrupole element, and the AC voltage may be six times the DC component. Upon scanning both AC and DC voltages while maintaining an approximate ratio of 6:1, a spectrum of ion abundance versus mass-to-charge ratio in atomic mass units (AMU) may be generated.

The chamber 102 includes electron emitters 113a, 113b at or proximal to a first end 114 of the chamber 102. The emitters 113a, 113b may be filament coils formed from a suitable filament material, such as tungsten or platinum, by conventional filament winding techniques. The filament coils may consist of a base metal such as iridium with a coating, such as yttrium dioxide, acting as the electron emitter. Of course, any appropriate electron source may be used. The electron emitters 113a, 113b provide a source of electrons to ionize gas molecules in the chamber 102 for detection by the sensor 100.

External circuitry (not shown) provides voltages to the rods 112a-112n via the buses (discussed above) to cause each of the quadrupole elements to be tuned for a particular ion having a specific Atomic Mass Unit (AMU) and mass-to-charge ratio. This causes the particular ion (if present) to travel toward a second end 116 of the chamber 102. Generally, other ions that may be present in the chamber 102 that do not have the same AMU and mass-to-charge ratio are pulled by the electric field from the channel to one of the rods 112a-112n and neutralized.

A plurality of ions 116 that reach the second end 118 of the chamber 102 that have a desired AMU and mass-to-charge ratio pass through a plurality of channels 122a-122n in the second end 116 to enter the second chamber 104. In an embodiment herein, the channels 122a-122n include metal tubes that are biased to cause the ions 118 to pass through the channels 122a-122n to enter the chamber 104. The ions 118 that enter the chamber 104 are detected by a detector 124 as described in more detail elsewhere herein. The number of ions of a particular AMU and mass-to-charge ratio striking the detector 124 when voltages on the rods 112a-112n are appropriately tuned is directly proportional to a number of gas molecules with the corresponding AMU and mass-to-charge ratio initially within the chamber 102. Consequently, by appropriately calibrating external electronics connected to the sensor 100, the user of the sensor 100 can determine not only what particular gas is present in the chamber 102, but also how much of the particular gas is present.

Figure 2:
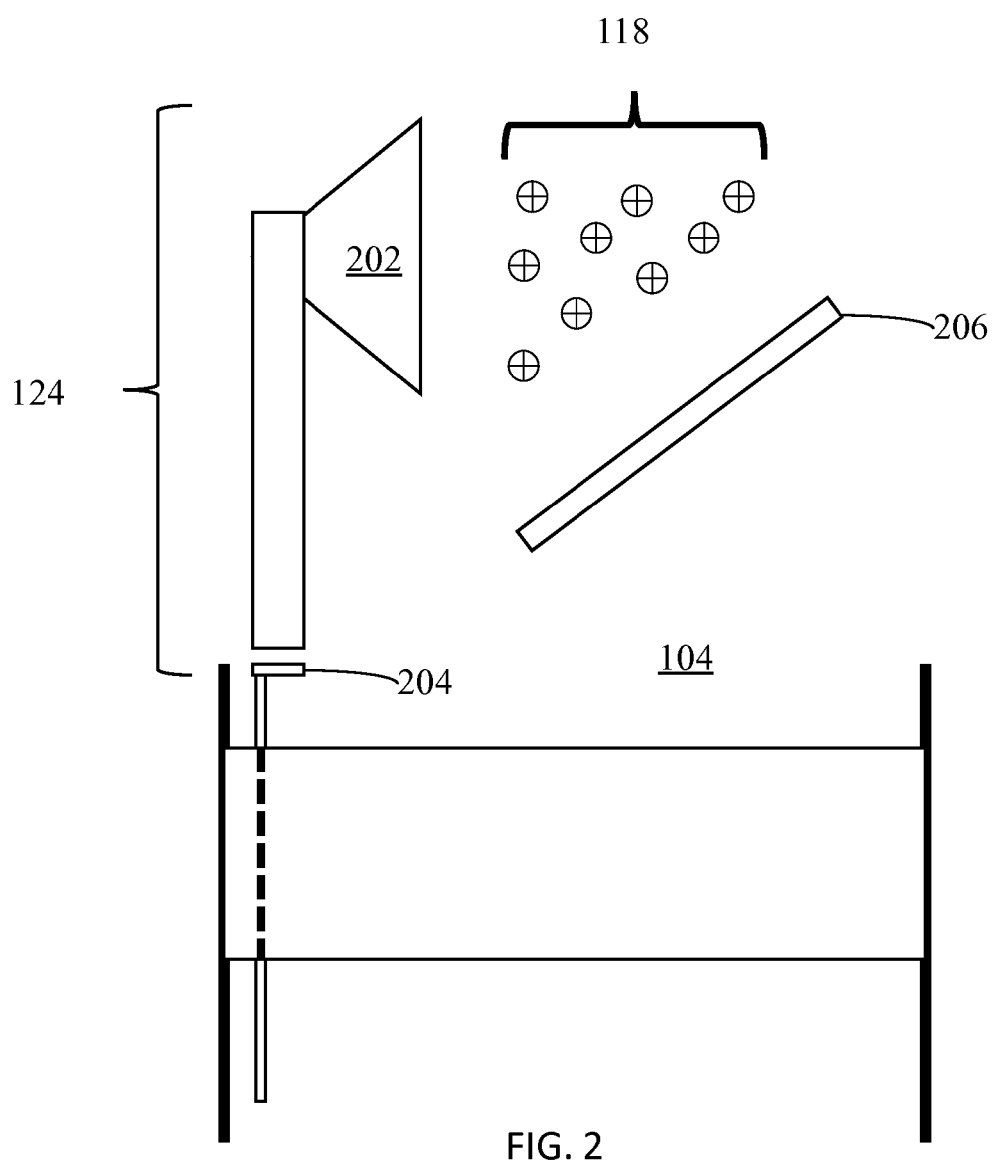
FIG. 2 is schematic diagram showing a miniature quadrupole mass filter arrays using an electron multiplier and detector according to an embodiment of the system described herein.

Referring to FIG. 2, an embodiment is shown where the detector 124 in the chamber 104 is provided by an electron multiplier 202 and a collector 204. The electron multiplier 202 may be a conventional electron multiplier using, for example a vacuum tube structure. The electron multiplier is mounted in an off-axis configuration which contributes to reducing noise caused by photons e.g. UV and other stray particles from the ion source. The electron multiplier 202 receives the ions 118 that pass through the channels 122a-122n and, as a result thereof, provide electrons to the collector 204. The amount of electrons provided to the collector 204 are proportional to the amount of ions received by the electron multiplier 202. Both the electron multiplier 202 and the collector 204 are conventional components known in the art. The collector 204 may extend to an outside portion of the chamber 104 to connect to conventional circuitry (not shown) that provides an indication of a number of electrons received by the collector 204. The circuitry may provide a signal to a receiving device (not shown) such as a display, a computer, etc. that may an indication to an operator and/or may save/record value(s) corresponding to the output of the collector 204.

In some embodiments, the chamber 104 may include a Faraday cup 206 that detects ions 118 while the electron multiplier 202 is turned OFF. This dual detection scheme is useful to calibrate the gain of the electron multiplier 202 using the Faraday Cup signal. In other embodiments, the Faraday cup 206 may not be present, in which case the ions 118 are detected entirely by the electron multiplier 202 and the collector 204.

Figure 3:
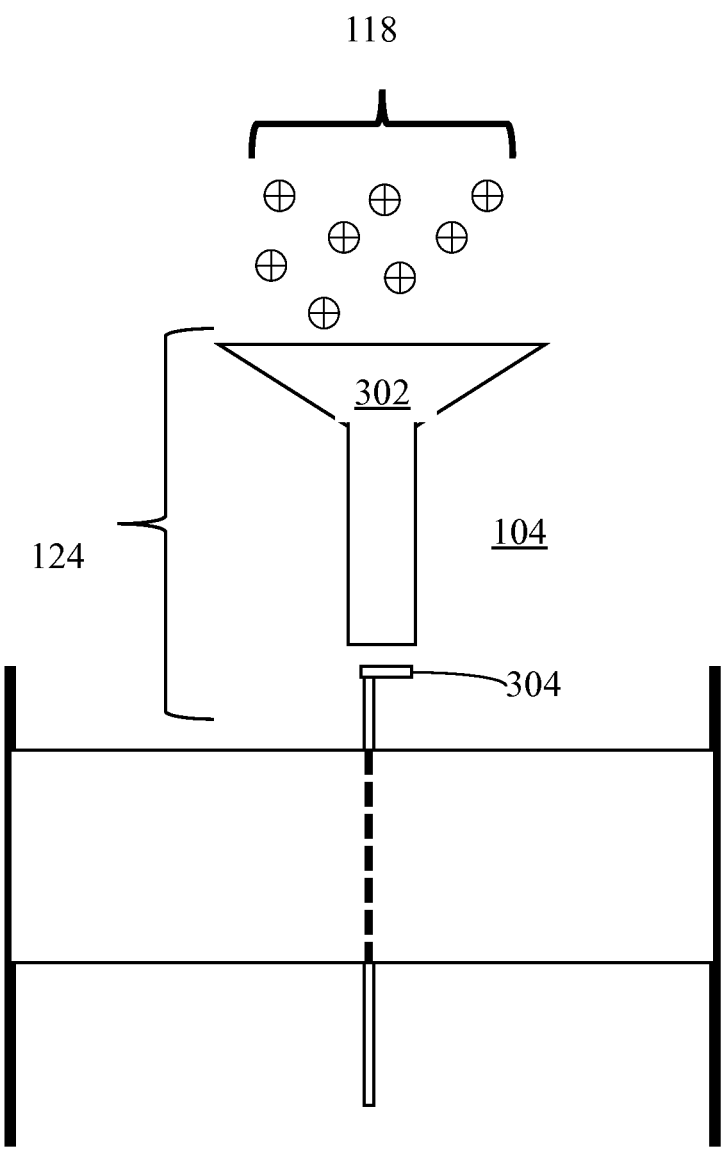
FIG. 3 is schematic diagram showing a miniature quadrupole mass filter arrays using an electron multiplier and detector provided on-axis with respect to a flow of electrons according to an embodiment of the system described herein.

Referring to FIG. 3, an alternative embodiment is shown with an electron multiplier 302 that is provided in the chamber 104 and on-axis with respect to the channels 122a-122n and the flow of the ions 118. As with the embodiment of FIG. 2, output from the electron multiplier 302 is provided to a collector 304 that is coupled to a circuit (not shown) that provides a display and/or data corresponding to the ions 118 that impinge the electron multiplier 302.

Figure 4:
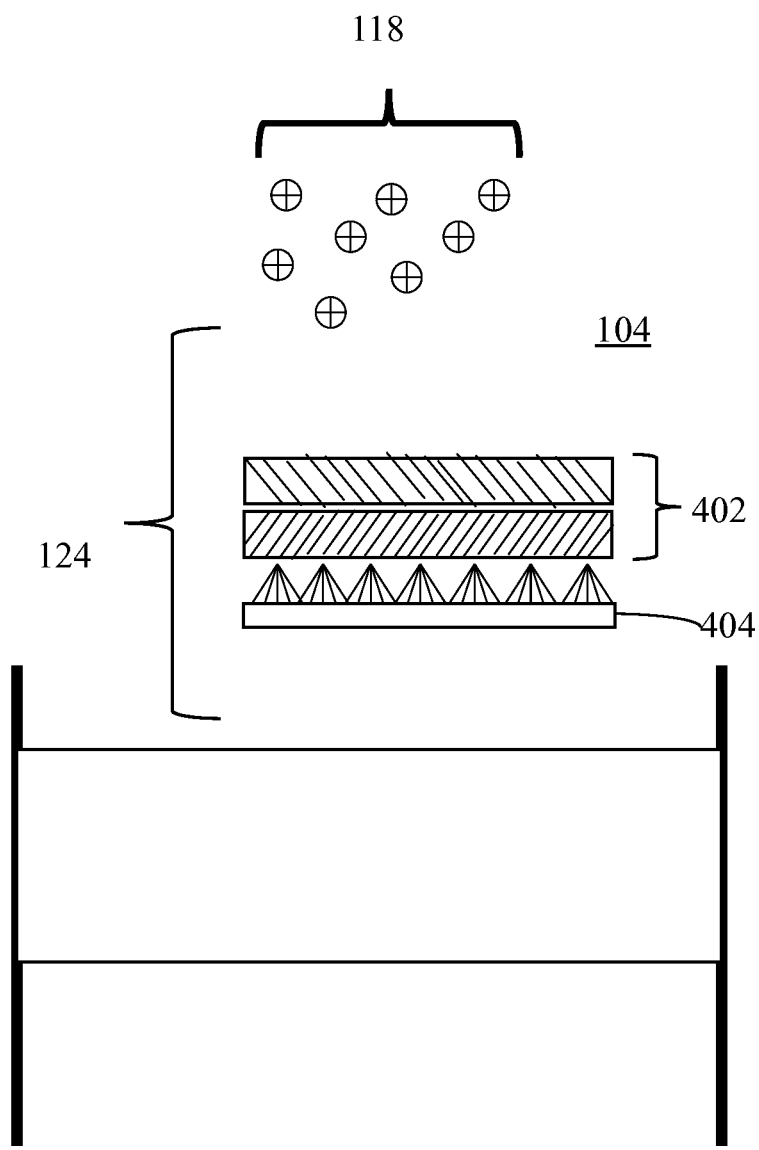
FIG. 4 is schematic diagram showing a miniature quadrupole mass filter arrays using a micro-channel plate and an electron detector according to an embodiment of the system described herein.

Referring to FIG. 4, a different embodiment is shown that uses a micro-channel plate device 402 that is provided on-axis in the chamber 104 and on-axis with respect to the channels 122a-122n and the flow of the ions 118. The micro-channel plate 402 may provide electrons in response to being impinged with the gas ions. As with the embodiment of FIG. 2 and FIG. 3, output from the micro-channel plate device 402 is provided to a collector 404 that is coupled to a circuit (not shown) that provides a display and/or data corresponding to the ions 118 that impinge the electron multiplier 402. The micro-channel plate device 402 may be a slab made from highly resistive material of typically 2 mm thickness with a regular array of tiny tubes or slots (micro-channels) leading from one face to an opposite face densely distributed over the whole surface. The micro-channels may be approximately ten micrometers in diameter and spaced apart by approximately fifteen micrometers.

FIG. 4 shows a stack of two microchannel plates 402 assembled in a chevron configuration, that is with angled channels rotated 180° from each other producing a chevron (v-like) shape. The angle between the channels reduces ion feedback in the device. In a chevron microchannel plate assembly the electrons that exit the first plate start the cascade in the next plate. The advantage of the chevron microchannel plate assembly over the straight channel microchannel plate assembly is significantly more gain at a given voltage. The two microchannel plates can either be pressed together or have a small gap between them to spread the charge across multiple channels.

Figure 5:
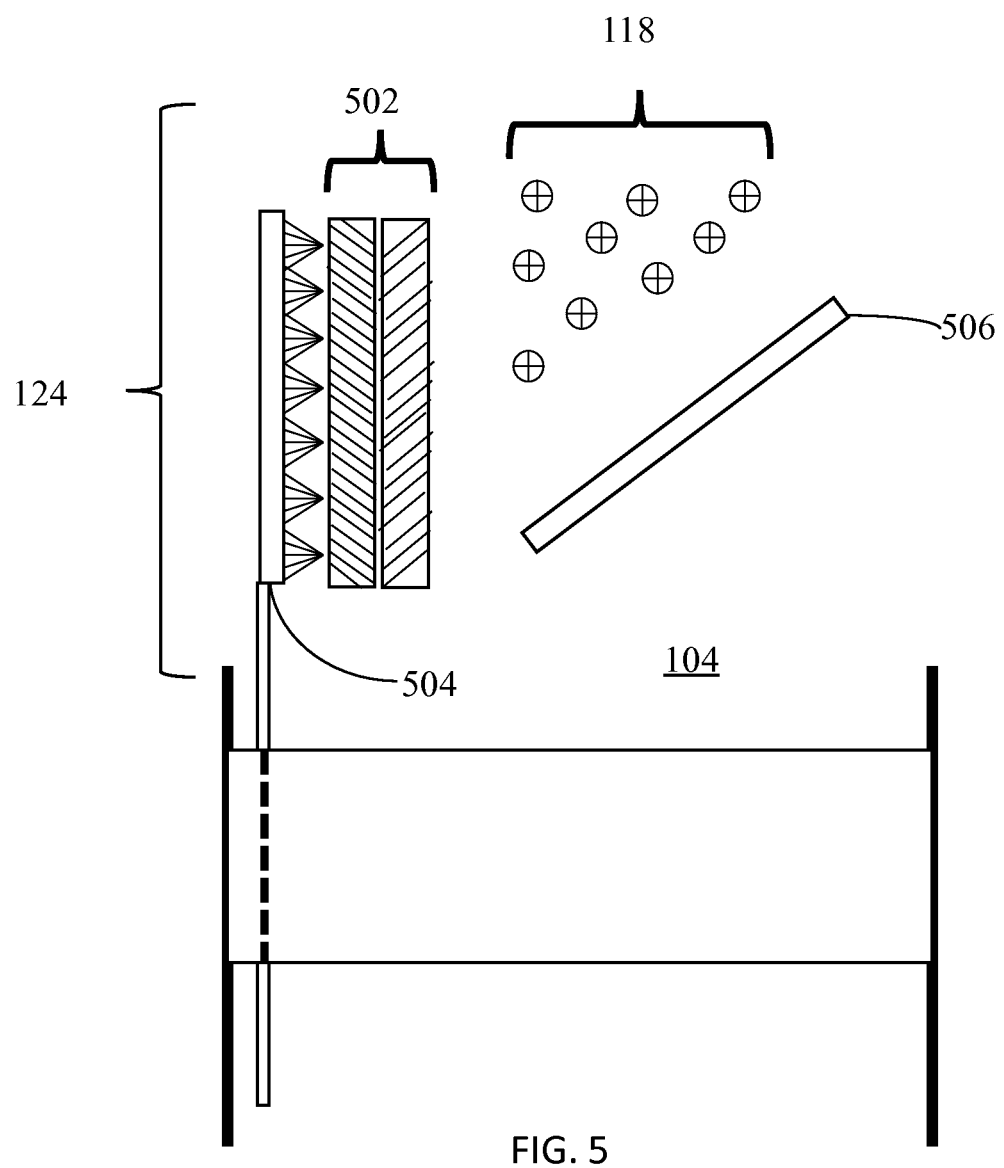
FIG. 5 is schematic diagram showing a miniature quadrupole mass filter arrays using a micro-channel plate and an electron detector provided off-axis with respect to a flow of electrons according to an embodiment of the system described herein.

Referring to FIG. 5, a different embodiment is shown using a micro-channel plate device 502 that is provided in the chamber 104 and is off-axis with respect to the channels 122a-122n and the flow of the ions 118. As with the embodiment of FIG. 2, FIG. 3, and FIG. 4, output from the micro-channel plate device 502 is provided to a collector 504 that is coupled to a circuit (not shown) that provides a display and/or data corresponding to the ions 118 that impinge the electron multiplier 502. Like the embodiment of FIG. 2, a Faraday cup 506 may optionally be used to detect the ions 118 that flow through the channels 122a-122n. In other embodiments, no Faraday cup is used even though the micro-channel plate device 502 is provided in the chamber 104 off-axis.

Various embodiments discussed herein may be combined with each other in appropriate combinations in connection with the system described herein. Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A gas sensor, comprising:
   a first chamber containing a plurality of evenly spaced rods having voltages with DC and AC voltage components having a same magnitude applied thereto to cause gas ions in the first chamber to move in a direction from a first end of the first chamber to a second end of the first chamber; and a second chamber coupled to the second end of the first chamber and having at least one ion detector, wherein ions pass from the first chamber to the second chamber through a plurality of channels between the first chamber and the second chamber and are detected by the at least one ion detector.

2. A gas sensor, according to claim 1, wherein the at least one ion detector includes one of: an electron multiplier and a micro-channel plate.

3. A gas sensor, according to claim 2, wherein the at least one ion detector is one of: on-axis and off-axis.

4. A gas sensor, according to claim 2, further comprising: a Faraday cup provided in the second chamber.

5. A gas sensor, according to claim 4, wherein the at least one ion detector is off-axis.

6. A gas sensor, according to claim 1, wherein the DC components of the first and second voltages are the same.

7. A gas sensor, according to claim 1, wherein the magnitude of the AC components is approximately six times a magnitude of the DC components.

8. A gas sensor, according to claim 1, wherein the AC voltage components have a same frequency and a relative phase of 180 degrees.

9. A gas sensor, comprising:
a first chamber containing a plurality of evenly spaced rods having voltages applied thereto to cause gas ions in the first chamber to move in a direction from a first end of the first chamber to a second end of the first chamber, wherein the voltages applied to the rods include a first voltage applied to a first subset of the rods and a second voltage applied to a second subset of the rods, each of first and second voltages containing a DC component and an AC component and wherein the DC components of the first and second voltages are the same and the AC components of the first and second voltages have a same frequency and magnitude and a relative phase of 180 degrees and wherein the magnitude of the AC components is approximately six times a magnitude of the DC components; and
a second chamber coupled to the second end of the first chamber and having at least one ion detector, wherein ions pass from the first chamber to the second chamber through a plurality of channels between the first chamber and the second chamber and are detected by the at least one ion detector.

10. A gas sensor, according to claim 9, wherein the at least one ion detector includes one of: an electron multiplier and a micro-channel plate.

11. A gas sensor, according to claim 10, wherein the at least one ion detector is one of: on-axis and off-axis.

12. A gas sensor, according to claim 10, further comprising:
a Faraday cup provided in the second chamber.

13. A gas sensor, according to claim 12, wherein the at least one ion detector is off-axis.

14. A method of operating a gas sensor, comprising:
applying voltages with DC and AC components to a plurality of evenly spaced rods in a first chamber to cause gas ions in the first chamber to move in a direction from a first end of the first chamber to a second end of the first chamber, wherein the DC and AC voltage components have a same magnitude;
passing ions from the first chamber into a second chamber coupled to the second end of the first chamber, the second chamber having at least one ion detector; and
detecting ions in the second chamber using the at least one ion detector.

15. A method, according to claim 14, wherein the at least one ion detector includes one of: an electron multiplier and a micro-channel plate.

16. A method, according to claim 15, wherein the at least one ion detector is one of: on-axis and off-axis.

17. A method, according to claim 16, wherein the at least one ion detector is a Faraday cup.

18. A method, according to claim 17, wherein the at least one ion detector is off-axis.

19. A method, according to claim 14, wherein the AC voltage components have a same frequency and a relative phase of 180 degrees.

* * * * *